United States Patent [19]

Arotin et al.

[11] Patent Number: 4,639,268

[45] Date of Patent: Jan. 27, 1987

[54] NITRO- AND CYANOGUANIDINES AS SELECTIVE PREEMERGENCE HERBICIDES AND PLANT DEFOLIANTS

[75] Inventors: Robert L. Arotin, Yardley, Pa.; Bryant L. Walworth, Pennington, N.J.; Michele E. Marini, Blacksburg, Va.

[73] Assignee: American Cyanamid Company, Stamford, Conn.

[21] Appl. No.: 759,703

[22] Filed: Jul. 29, 1985

[51] Int. Cl.$^4$ .................... A01N 37/34; A01N 33/04
[52] U.S. Cl. ........................... 71/105; 71/121; 71/70; 564/104; 564/230
[58] Field of Search ................... 71/105, 121

[56] References Cited

U.S. PATENT DOCUMENTS 4,468,246 8/1984 Pallos .................... 71/100

Primary Examiner—Catherine L. Mills
Attorney, Agent, or Firm—Alice C. Brennan

[57] ABSTRACT

There are provided novel nitroguanidine and cyanoguanidine compounds. A method of dessicating and defoliating plants by applying to the foliage thereof certain nitroguanidine or cyanoguanidine compounds and a method for the selective preemergence control of undesirable broadleaf weeds and grasses in the presence of graminaceous crops are disclosed.

10 Claims, No Drawings

NITRO- AND CYANOGUANIDINES AS SELECTIVE PREEMERGENCE HERBICIDES AND PLANT DEFOLIANTS

This invention relates to certain novel nitroguanidine and cyanoguanidine compounds. It also relates to a method of desiccating and defoliating plants, particularly malvaceous plants such as cotton, by applying to the foliage thereof an effective amount of a nitroguanidine or cyanoguanidine compound. It further relates to a method for the selective preemergence control of undesirable broadleaf weeds and grasses in the presence of graminaceous crops, by applying a herbicidally effective amount of a nitro- or cyanoguanidine to soil containing the seeds of the planted crop and seeds or other propagating organs of undesirable plants.

Although certain nitro- and cyanoguanidines are known, to the best of our knowledge, such compounds have not been disclosed or suggested as selective preemergence herbicidal agents effective for the control of undesirable weeds and grasses in the presence of graminaceous crops or as desiccants or defoliants for cotton and other plants. Rather, some nitroguanidines are described by A. F. McKay et al., U.S. Pat. No. 2,559,085, issued July 3, 1951, as intermediates for the preparation of synthetic antibiotics, antihistamines and insecticides. Others are described by R. A. Henry et al., in U.S. Pat. No. 2,946,820, issued July 26, 1980, the preparation of high bulk density nitroguanidines with improved handling characteristics, and still others are described by L. M. Speltz, B. L. Walworth and A. D. Pavlista in the American Cyanamid Patent Application, Publication No. DE 3345-281-A; 84-159685/26; Priority Document U.S. patent application Ser. No. 451,698, Dec. 20, 1982, abandoned. The above application describes the use of nitroguanidines and cyanoguanidines as yield enhancing agents for crops such as potatoes, sugar beets, barley, wheat and even cotton. It also describes generically some α-substituted nitro- and cyanoguanidines. However, it does not specifically identify or describe the novel α-substituted nitro- and cyanoguanidines of the present invention, nor does it suggest that application of nitroguanidines and cyanoguanidines to malvaceous plants especially cotton with at least 60% open boll one to two weeks prior to harvest will provide controlled defoliation of the plants and permit easier harvesting of the crop. Furthermore, the L. M. Speltz et al. application does not disclose the use of nitroguanidines or cyanoguanidines as preemergence herbicides nor do they suggest that such compounds exhibit selectivity in graminaceous crops.

When cotton is harvested, contamination of the seed cotton (seed plus lint) by green leaves and petioles hinders the harvesting procedure and lowers cotton lint quality by staining the lint. However, with the novel compounds and method of the present invention, mature cotton plants can now be treated with an effective amount of a selected nitroguanidine or cyanoguanidine prior to harvest, thereby inducing the cotton leaves to fall cleanly from the plant (defoliation) prior to harvest. This facilitates an easier harvest and provides a high quality lint essentially free of chlorophyll stains.

While it is well recognized that controlled defoliation of cotton and other plants could provide the above-mentioned advantages, surprisingly, there are but few chemicals that have met with commercial success as defoliating agents and even these compounds are not entirely satisfactory. They include: N-(substituted phenyl)-N-1,2,3-thiadiazole-5-yl ureas; tributyl phosphorotrithioate; sodium chlorate; and O,O,O,O-tetraethyl dithiopyrophosphate.

It is therefore an object of the present invention to provide novel nitroguanidine and cyanoguanidine compounds that are highly effective as preemergence herbicides, desiccants and defoliants for plants.

It is also an object of this invention to provide a method for the selective preemergence control of undesirable broadleaf weeds and grasses in the presence of graminaceous crops, such as corn, wheat, barley and rice.

It is a further object of this invention to provide a method for defoliating cotton plants prior to harvest thereby facilitating easier harvesting of the cotton and providing high quality cotton lint essentially free of stains.

These and other objects of the present invention will become clearer from the more detailed description of the invention which follows.

SUMMARY OF THE INVENTION

The invention described herein relates to novel herbicidal and plant defoliating and/or desiccating nitro- and cyanoguanidine compounds represented by the following structural formula (I):

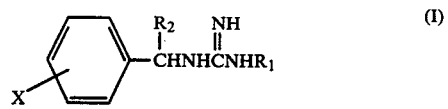

wherein $R_1$ is $NO_2$ or $CN$; $R_2$ is $n\text{-}C_3H_7$, $CH_2OCH_3$ or $CH_2CH=CH_2$; X is hydrogen, ortho-, meta- or para-fluoro, meta-methoxy, meta-hydroxy or para-chloro; and the salts, tautomers and optical isomers thereof and the (+) or (−)-isomers of compounds having the above structure, where $R_1$ and X are as described above and $R_2$ is $CH_3$, $C_2H_5$ or $CF_3$.

The invention also relates to a method for defoliating plants, particularly cotton, by applying to the foliage thereof a defoliatingly effective amount of a nitroguanidine or cyanoguanidine having the general structural formula (II):

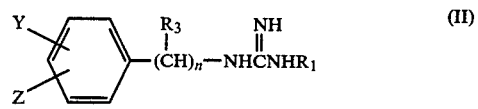

wherein $R_1$ is $NO_2$ or $CN$; $R_3$ is allyl, $CF_3$, $CH_2OCH_3$ or $C_1\text{-}C_3$ alkyl optionally substituted with OH or $OCH_3$; Y is hydrogen, halogen or $OR_4$ where $R_4$ is hydrogen or $C_1\text{-}C_4$ alkyl; Z is hydrogen, halogen, $CH_3$ or $CF_3$; n is an integer of 0 or 1, and the salts, tautomers and optical isomers thereof.

PREFERRED EMBODIMENTS OF THE INVENTION

A preferred group of nitroguanidines and cyanoguanidines useful as selective preemergence herbicides for use in the presence of graminaceous crops has the Formula I structure, wherein $R_1$ and X are as described above; and $R_2$ is $CH_2CH=CH_2$ or $CH_2OCH_3$; and the salts, tautomers and optical isomers thereof.

A preferred group of nitro- and cyanoguanidine compounds which are effective as defoliating agents have the Formula II structure, wherein $R_1$ is as described above; $R_3$ is allyl, $CF_3$, $CH_2OCH_3$ or alkyl $C_1$–$C_3$; n is 1; Y is hydrogen, Cl, Br or $OCH_3$; Z is hydrogen, Br, Cl, $CH_3$ or $CF_3$; and the salts, tautomers and optical isomers thereof.

Salts of the nitro and cyanoguanidines useful as defoliants when applied in accordance with the method of the present invention, include the inorganic alkali metal, alkaline earth metal, Co, Cu, Zn, and Ag salts, together with the organic amine salts represented by the structure, $^+NR_aR_bR_cR_d$, wherein $R_a$, $R_b$, $R_c$, and $R_d$ are each selected from hydrogen and alkyl $C_1$–$C_{30}$ straight or branched chain and optionally substituted with one or two —OH, $C_3$–$C_6$ alkenyl or $C_3$–$C_6$ alkynyl groups. Preferred salts of these compounds include the sodium, calcium, magnesium, potassium, ammonium, methylamine, trimethylamine, dodecylamine, tributylamine, diisopropylamine, triethylamine, tetrabutylamine, and tallow-amine salts.

These salts are readily prepared by dissolving or dispersing the appropriate nitroguanidine or cyanoguanidine as depicted by both Formula I and Formula II above in an aqueous solution or suspension of an alkali metal hydroxide, alkaline earth metal hydroxide, organic ammonium hydroxide or the like.

The substituted phenylnitroguanidines, encompassed by Formula I and II, are useful in the method of the present invention and can be prepared by reaction of an appropriately substituted aniline with approximately an equimolar amount of an N-alkyl-N-nitroso-N'-nitroguanidine in the presence of an aqueous alcoholic solution. The mixture is heated to about 40° C., treated with a strong base such as sodium hydroxide, and the alcohol removed from the mixture by evaporation. The remaining liquid is then filtered, and the filtrate acidified with a strong mineral acid (i.e., hydrochloric acid) to yield the desired substituted phenylnitroguanidine. This reaction is graphically illustrated as follows:

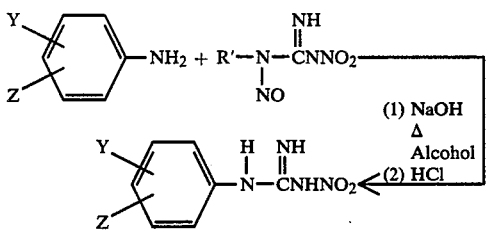

wherein R' is $C_1$–$C_4$ alkyl; and Y and Z are as described above. (See McKay and Wright [Journal American Chemical Society, 71:1968 (1949)]).

Alternatively, the Formula I benzylnitroguanidines can be prepared by reacting approximately equimolar amounts of the appropriate benzylamine with a 1-alkyl-3-nitro-1-nitrosoguanidine in the presence of an aqueous aliphatic alcohol. The reaction may be illustrated as follows:

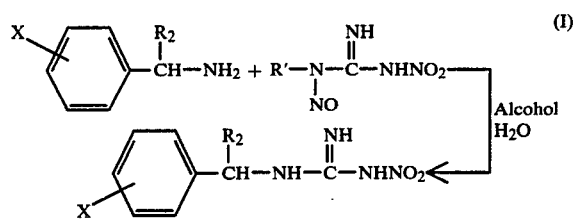

wherein $R_2$ is $CH_3$, $C_2H_5$, n-$C_3H_7$, $CF_3$, $CH_2OCH_3$ or $CH_2CH=CH_2$ and X is hydrogen, fluoro, chloro, methoxy or hydroxy.

Preparation of the substituted phenyl and benzyl cyanoguanidines is readily accomplished by dissolving or dispersing the appropriately substituted aniline or benzylamine in hydrochloric acid and admixing the thus-formed solution or dispersion with an equimolar amount of sodium dicyanamide. In practice, it is generally desirable to disperse the sodium dicyanamide in water prior to admixture with the aniline solution or to disperse the sodium dicyanamide in ethoxyethanol for reaction with the benzylamine. This reaction is illustrated as follows:

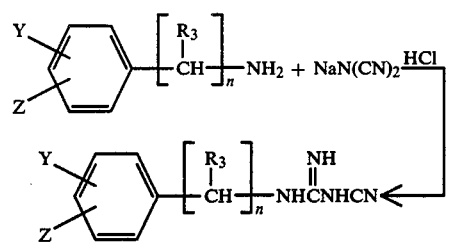

wherein Y is hydrogen, halogen, or $OR_4$; $R_4$ is hydrogen or $C_1$–$C_4$ alkyl; Z is hydrogen, halogen, $CH_3$ or $CF_3$; n is an integer of 0 or 1 and $R_3$ is allyl, $CF_3$ or $C_1$–$C_3$ alkyl optionally substituted with OH, or $OCH_3$.

While the nitroguanidines and cyanoguanidines, effective as preemergence herbicidal agents and as defoliating agents for plants, are shown in one tautomeric form, by Formulas I and II, i.e.

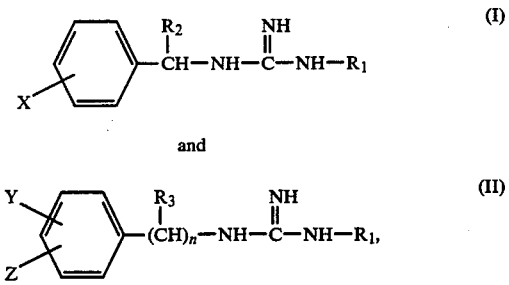

wherein $R_1$, $R_2$, $R_3$, X, Y and Z are as described above; it should be recognized that these compounds may actually exist in different tautomeric forms, such as:

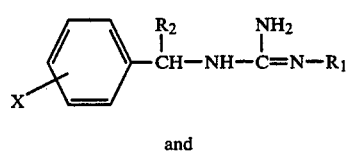

and

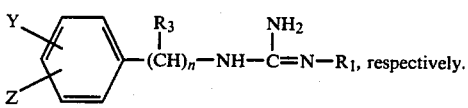

As tautomers differ from each other only in the position of the hydrogen atom and double bond and ordinarily exist together in equilibrium, it is intended that all tautomeric forms of the Formula I and II compounds be included in the invention of the subject application.

The nitro- and cyanoguanidines useful in the method of the present invention are particularly suitable for desiccating and defoliating cotton plants. In practice it is generally found that from about 0.001 to 10 kg per hectare and preferably about 0.01 to 4 kg per hectare, of a Formula I or Formula II compound, applied to the foliage of cotton as a dilute solid or liquid formulation when approximately 60% of the bolls are open and about 1 to 2 weeks before harvest will desiccate the plants, induce the plants to shed their leaves and inhibit regrowth.

The nitro- and cyanoguanidines of this invention are also useful as preemergence herbicidal agents, particularly selective herbicidal agents useful for controlling broadleaf weeds and grasses in the presence of graminaceous crops. In this use, the active ingredients are applied to soil in which the graminaceous crops have been planted. Generally, about 1.0 to 10 kg/ha and preferably about 1.0 to 4.0 kg/ha, applied as a dilute solid compositions, such as a granular formulation, dust or dust concentrate, or a liquid spray such as an aqueous dispersion or suspension of a flowable concentrate, wettable powder or emulsifiable concentrate, is effective for controlling a wide variety of broadleaf weeds and grasses, without injuring the crop.

The compounds of this invention may be used alone or in combination or conjunction with defoliants including N-(substituted phenyl)-N-1,2,3-triadiazole-5-yl ureas; tributyl phosphorotrithioate; sodium chlorate; 2-(2-imidazolin-2-yl)quinolines; 2-(2-imidazolin-2-yl)-pyridines; O,O,O',O-tetraethyl dithiopyrophosphate; and 2,1,3-benzothiadiazole-dicarbonitriles.

The 2-(2-imidazolin-2-yl)pyridines and 2-(2-imidazolin-2-yl)quinolines that can be used in combination with the nitro- and cyanoguanidines of the invention include:

methyl 2-(5-isopropyl-5-methyl-4-oxo-2-imidazolin-2-yl)nicotinate;
2-(5-isopropyl-5-methyl-4-oxo-2-imidazolin-2-yl)-nicotinic acid;
calcium 2-(5-isopropyl-5-methyl-4-oxo-2-imidazolin-2-yl)nicotinate;
2-propynyl 2-(5-isopropyl-5-methyl-4-oxo-2-imidazolin-2-yl)nicotinate;
furfuryl 2-(5-isopropyl-5-methyl-4-oxo-2-imidazolin-2-yl)nicotinate;
sodium 2-(5-isopropyl-5-methyl-4-oxo-2-imidazolin-2-yl)nicotinate;
isopropylammonium 2-(5-isopropyl-5-methyl-4-oxo-2-imidazolin-2-yl)nicotinate;
5-ethyl-2-(5-isopropyl-5-methyl-4-oxo-2-imidazolin-2-yl)nicotinic acid;
6-chloro-2-(5-isopropyl-5-methyl-4-oxo-2-imidazolin-2-yl)nicotinic acid;
6-methyl-2-(5-isopropyl-5-methyl-4-oxo-2-imidazolin-2-yl)nicotinic acid;
2-(5-isopropyl-5-methyl-4-oxo-2-imidazolin-2-yl)-3-quinolinecarboxylic acid;
2-(5-isopropyl-5-methyl-4-oxo-2-imidazolin-2-yl)-7-methyl-3-quinolinecarboxylic acid;
2-(5-isopropyl-5-methyl-4-oxo-2-imidazolin-2-yl)-6-methyl-3-quinolinecarboxylic acid;
chloro-2-(5-isopropyl-5-methyl-4-oxo-2-imidazolin-2-yl)-3-quinolinecarboxylic acid;
3,7-chloro-2-(5-isopropyl-5-methyl-4-oxo-2-imidazolin-2-yl)-3-quinolinecarboxylic acid;
5,7-dihydro-α-isopropyl-α-methyl-5,7-dioxo-6H-pyrrolo[3,4-b]pyridine-6-acetonitrile;
α-cyclopropyl-5,7-dihydro-α-methyl-5,7-dioxo-6H-pyrrolo[3,4-b]pyridine-6-acetonitrile;
5,7-dihydro-α-isopropyl-2-methoxy-α-methyl-5,7-dioxo-6H-pyrrolo[3,4-b]pyridine-6-acetonitrile;
1,3-dihydro-α-isopropyl-α-methyl-1,3-dioxo-2H-pyrrolo[3,4-b]quinoline-2-acetonitrile;
2-chloro-5,7-dihydro-α-isopropyl-α-methyl-5,7-dioxo-6H-pyrrolo[3,4-b]pyridine-6-acetonitrile;
1,3-dihydro-α-isopropyl-α-methyl-1,3-dioxo-2H-pyrrolo[3,4-b]quinoline-2-acetamide;
2-chloro-5,7-dihydro-α-isopropyl-α-methyl-5,7-dioxo-6H-pyrrolo[3,4-b]pyridine-6-acetamide;
5,7-dihydro-α-isopropyl-2-methoxy-α-methyl-5,7-dioxo-6H-pyrrolo[3,4-b]pyridine-6-acetamide;
3-bromo-5,7-dihydro-α-isopropyl-α-methyl-5,7-dioxo-6H-pyrrolo[3,4-b]pyridine-6-acetamide;
5,7-dihydro-α-isopropyl-α-methyl-5,7-dioxo-6H-pyrrolo[3,4-b]pyridine-6-acetamide;
3-isopropyl-8-methoxy-3-methyl-5H-imidazo[1'.2':1,2]-pyrrolo[3,4-b]pyridine-2-(3H),5-dione;
3-isopropyl-3-methyl-5H-imidazo[1',2':1,2]pyrrolo-[3,4-b]pyridine-2(3H),5-dione;
2-isopropyl-2-methyl-5H-imidazo[1',2':1,2]pyrrolo-[3,4-b]pyridine-3(2H),5-dione;
2-isopropyl-2-methyl-5H-imidazo[1',2':1,2]pyrrolo-[3,4-b]quinoline-3(2H),5-dione;
methyl 2-[(carbamoyl-1,2-dimethylpropyl)carbamoyl]-quinoline-3-carboxylate;
methyl 2-[(1-carbamoyl-1,2-dimethylpropyl)carbamoyl]-nicotinate;
benzyl 2-[(1-carbamoyl-1-methylpropyl)carbamoyl]-nicotinate; and
dodecyl 2-[(1-carbamoyl-1,2-dimethylpropyl)carbamoyl)-nicotinate.

The nitroguanidines and cyanoguanidines of this invention may also be used in combination or conjunction with other pest control agents such as insecticidal agents, fungicides and pesticidal synergists such as piperonyl butoxide.

The insecticides contemplated for use in combination treatments with the nitroguanidines and cyanoguanidines of this invention include:

S-6-chloro-2,3-dihydro-2-oxobenzoxazol-3-yl-methyl O,O-diethyl phosphorodithioate;
N,N-dimethyl-2-methylcabamoyloximino-2-(methylthio)acetamide;
1-methylethyl (E,E)-11-methoxy-3,7-11-trimethyl-2,4-dodecadienoate;
S-2,3-dihydro-5-methoxy-2-oxo-1,3,4-thiadiazol-3-ylmethyl O,O-dimethyl phosphorodithioate;
O,S-dimethyl phosphoramidothioate;
2-(diethoxyphosphinylimino)-4-methyl-1,3-dithiolane;
(RS)-α-cyano-3-phenoxybenzyl N-(2-chloro-α,α,α-trifluoro-p-tolyl)-D-valinate;
4-chlorophenyl-3-(2-6-difluorobenzolylures;

O,O-diethyl O-3,5,6-trichloro-2-pyridyl phosphorothioate;
N'-(4-chloro-2-methylphenyl)-N,N-dimethylmethanimidamide;
1,3-di(carbamoylthio)-2-dimethylaminopropane;
N-methylbis(2,4-xyliminomethyl)amine;
O,S-dimethyl acetylphosphoramidothioate;
O,O-diethyl S-p-chlorophenylthiomethyl phosphorodithioate;
6,7,8,9,10,10-hexachloro-1,5,5a,6,9,9a-hexahydro-6,9-methano-2,4,3-benzodioxathiepin-3-oxide;
2,4,5,4'-tetrachlorodiphenyl sulphone;
alpha-methylbenzyl 3-(dimethoxyphosphinyloxy)cis-chrotomate;
2-(2-butoxyethoxy)ethyl ester;
bis(dialkylphosphinothionyl)disulfide;
O,O-dimethyl O-2-chloro-4-nitrophenyl phosphorodithioate;
(S)-α-cyano-3-phenoxybenzyl (IR)-cis-3-(2,2-dibromovinyl)-2,2-dimethylcyclopropanecarboxylate;
(±)-α-cyano-4-fluoro-3-phenoxybenzyl (+)-4-difluoromethoxy-α-(1-methylethyl)benzeneacetate;
(RS)-α-cyano-4-fluoro-3-phenoxybenzyl;
(IRS)-cis, trans-3-(2,2-dichlorovinyl-2,2-dimethylcyclopropanecarboxylate;
S-methyl N-(methylcarbamoyloxy)thio-acetimidate;
2,3-dihydro-2,2-dimethyl-7-benzofuranyl-methylcarbamate;
2-methyl-2-(methylthio)propanol O-[(methylamino)carbonyl]oxime;
O,O-diethyl-S-(tert-butylthiomethyl)phosphorodithioate;
O,O-dimethyl S-phthalimidomethyl phosphorodithioate;
O-2,4-dichlorophenyl O-ethyl S-propyl phosphorodithioate;
O-4-bromo-2-chlorophenyl O-ethyl S-propyl phosphorothioate;
2-(dimethylamino-5,6-dimethyl-4-pyrimidinyl dimethylcarbamate;
dimethyl 2,2-dichlorovinyl phosphate;
dimethyl-1,2-dibromo-2,2-dichloroethyl phosphate;
2,4-dinitro-6-(2-octyl)phenyl crotonate;
dimethyl 2-chloro-2-diethylcarbamoyl-1-methyl vinyl phosphate;
N-methyl-1-naphthyl carbamate;
O,O-diethyl-S-(ethylthiomethyl)phosphorodithioate;
O,O-dimethyl-S-(ethylthiomethyl)phosphorodithioate;
O,O-dimethyl S-(4-oxobenzotriazine-3-methyl)-phosphorodithioate;
2,3-p-dioxane S,S-bis(O,O-diethylphosphorodithioate);
O,O-diethyl O-(2-isopropyl-4-methyl-6-pyrimidinyl)-phosphorothioate;
O,O-dimethyl S-(N-methylcarbamoylmethyl)phosphorodithioate;
O,O-diethyl O-p-nitrophenyl phosphorothioate;
O,O-dimethyl O-p-nitrophenyl phosphorothiate;
O,O-dimethyl O-(3-methyl-4-nitrophenyl)thionophosphate;
O,O-dimethyl S-p-chlorophenylthiomethyl phosphorodithioate;
methyl-4-dimethylamino-3,5-xylyl carbamate;
2,2-bis(p-chlorophenyl)-1,1,1-trichloroethane;
dichlorodiphenyl dichloroethane;
chlorinated camphene;
terpene polychlorinate;
O,O,O',O'-tetramethyl-O,O'-thiodi-p-phenylene phosphorothioate;
O,O,O',O'-tetraethyl S,S'-methylene bis-phosphorodithioate;
dimethyl 2-methoxycarbonyl-1-methylvinyl phosphate;
diethyl(dimethoxyphosphinothioylthio)succinate;
O,O-dimethyl O-[3-methyl-4-(methylthio)phenyl]-phosphorothioate;
(RS)-α-cyano(3-phenoxyphenyl)methyl (RS)-4-chloro-α-(1-methlethyl)benzeneacetate;
(RS)-α-cyano(3-phenoxyphenyl)methyl (1RS)-cis,-trans-3-(2,2-dichloroethenyl)-2,2-dimethyl cyclopropanecarboxylate;
(±)-α-cyano(3-phenoxyphenyl)methyl (+)-4-(difluoromethoxy)-α-(1-methylethyl)benzenacetate;
(3-phenoxyphenyl)methyl (1RS)-cis,trans-3-(2,2-dichloroethenyl)-2,2-dimethylcyclopropanecarboxylate;
2,2-bis(p-methoxyphenyl-1,1,1,-tri-chloroethane;
4,4'-dichloro-α-trichloromethylbenzhydrol; and
3-(dimethoxyphosphinyloxy)-N,N-dimethyl-cis-crotonamide.

Advantageously, the compounds of the present invention can be formulated as solid or liquid compositions which may be dispersed in a liquid or solid diluent for application to the foliage of plants or to soil in which they are grown. The substituted guanidines of the invention may be formulated as flowable concentrates, emulsifiable concentrates, wettable powders, dusts or dust concentrates.

A typical emulsifiable concentrate can be prepared by dissolving, on a weight basis, about 8% of the active guanidine in about 40% of N-methylpyrrolidone, about 35% of a mixture of substituted benzenes, and about 10% of a spreader activator, having ingredients alkylarylpolyoxyethylene glycol, free-fatty acid and propanol, with about 7% by weight of a nonionic surfactant, such as octylphenoxy polyethoxy ethanol, and nonylphenoxy polyethoxy ethanol. This concentrate is dispersed in water for application as a liquid spray.

Emulsifiable concentrates can also be prepared by dissolving, on a weight basis, about 10% of the active guanidine in about 58% of N-methylpyrrolidone, about 24% octyl alcohol, and about 8% polyoxyethylated castor oil.

Flowable liquid concentrates can be prepared by grinding together about 40%, by weight, of the substituted nitro- or cyanoguanidine, about 0.40% colloidal magnesium aluminum silicate, about 1.50% sodium salts of polymerized alkyl naphthalene sulfonic acids, about 8.0% propylene glycol, about 0.1% ethoxylated octylphenol, about 0.1% nonylphenoxy polyethoxy ethanol, about 0.07% citric acid, about 0.06% xanthan gum, about 0.10% paraformaldehyde and about 49.77% water.

Flowable liquid concentrates can be prepared by milling together about 46%, by weight, of the substituted guanidine with about 0.4%, by weight, of colloidal magnesium aluminum silicate, about 1.5%, by weight, of naphthalene formaldehyde condensate, about 8%, by weight, of polyethylene glycol, about 0.1%, by weight, of nonylphenol ethylene oxide condensate (9–11 moles ethylene oxide), about 0.1%, by weight, of a dispersing agent (e.g., sodium lignosulfonate), about 0.07%, by weight, citric acid, about 46%, by weight, of water, and about 0.06%, by weight, of xanthan gum. This concentrate is dispersed in water for application as a liquid spray.

A typical wettable powder can be prepared by grinding together, on a weight basis, about 20% to 45% of a finely-divided carrier (e.g., kaolin, bentonite, diatomaceous earth, and attapulgite), about 45% to 80% of the active compound, about 2% to 5% of a dispersing agent (e.g., sodium lignosulfonate), and about 2% to 5% of a nonionic surfactant (e.g., octylphenoxy polyethoxy ethanol, and nonylphenoxy polyethoxy ethanol). This formulation is generally dispersed in water for application as a liquid spray.

The following non-limiting examples are presented for the purpose of illustrating the present invention and facilitating a better understanding thereof. Unless otherwise noted, all parts are by weight.

EXAMPLE 1

Preparation of 1-(α-Ethylbenzyl)-3-nitroguanidine

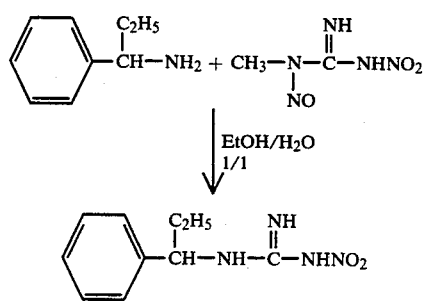

α-Ethylbenzylamine (7.2 g, 0.053 m) is added dropwise at room temperature to a slurry of 1-methyl-3-nitro-1-nitrosoguanidine (7.8 g, 0.053 m) in 200 mL of EtOH/H$_2$O (1/1). After stirring the mixture at room temperature for 18 hours, the precipitate which forms is removed by filtration, washed with EtOH/H$_2$O (30/70) and air dried. Recrystallization from CH$_2$Cl$_2$/CH$_3$OH (98/2) gives 9.5 g (82%) of a white solid with mp 129.5°–130.5° C.

Elemental Analysis: N$_4$O$_2$C$_{10}$H$_{14}$ M.W. 222.24.
Calculated: C-54.04%; H-6.35%; N-25.21%.
Found: C-54.06%; H-6.42%; N-25.36%.

Following the above procedure but substituting the appropriate α-substituted benzylamine for α-ethylbenzylamine yields the following compounds:

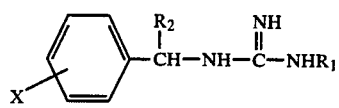

| X | R$_1$ | R$_2$ | mp °C. | |
|---|---|---|---|---|
| H | NO$_2$ | CH$_3$ | 115–116.5 | |
| 2-F | NO$_2$ | CH$_3$ | 99–102 | |
| 4-F | NO$_2$ | CH$_3$ | 133–136 | |
| H | NO$_2$ | CH$_3$ | 126–127 | (+)-isomer |
| 3-OCH$_3$ | NO$_2$ | CH$_3$ | 126–130 | |
| H | NO$_2$ | CF$_3$ | 149–151 | |
| H | NO$_2$ | C$_2$H$_5$ | 100–105 | (−)-isomer |
| 3-F | NO$_2$ | CH$_3$ | 135–138 | |
| H | NO$_2$ | C$_2$H$_5$ | 105–107 | (+)-isomer |
| H | NO$_2$ | n-C$_3$H$_7$ | 129–131 | |
| H | NO$_2$ | CH$_2$CH=CH$_2$ | 121–123 | |
| 3-OCH$_3$ | NO$_2$ | C$_2$H$_5$ | 115–117 | |
| 3-F | NO$_2$ | C$_2$H$_5$ | 135–137 | |
| 4-F | NO$_2$ | C$_2$H$_5$ | 82–87 | |
| 3-Cl | NO$_2$ | C$_2$H$_5$ | 115–118 | |
| 4-Cl | NO$_2$ | C$_2$H$_5$ | semi-solid | |
| H | NO$_2$ | CH$_2$OCH$_3$ | 167–168 | |
| H | NO$_2$ | CH$_3$ | 127.5–128 | (−)-isomer |
| 2-OCH$_3$ | NO$_2$ | CH$_3$ | 188–192 | |
| 3-CH$_3$ | NO$_2$ | CH$_3$ | 140–143 | |
| 3-CF$_3$ | NO$_2$ | C$_2$H$_5$ | 128–132 | |
| 4-OCH$_3$ | NO$_2$ | C$_2$H$_5$ | 94–97 | |

EXAMPLE 2

Preparation of 1-cyano-3-(α-ethylbenzyl)guanidine

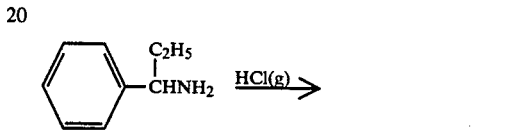

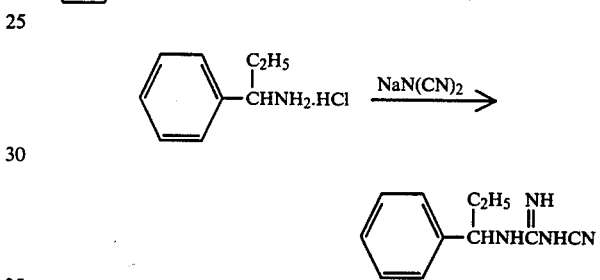

13.5 g (0.1 mol) α-Ethylbenzylamine dissolved in 200 mL anhydrous ether is treated with excess hydrogen chloride and stirred for 1 hour. Solids are isolated by filtration, washed well with ether and dried overnight under vacuum. A mixture of 10.8 g (0.063 mol) of the hydrochloride, 5.6 g (0.063 mol) sodium dicyanamide and 100 mL 1-butanol is heated to reflux. Water (12 mL) is added dropwise over a 50 minute period to give a solution. After refluxing for 24 hours, the solution is vacuum stripped and the residue chromatographed on flash column silica gel using ethyl acetate as eluent. The appropriate fractions are concentrated to a gummy solid which is triturated with ether and hexanes and then dried under vacuum to give a white solid weighing 8.85 g (69.4%) with mp 121°–123°.

| | % C | % H | % N |
|---|---|---|---|
| Calcd. | 65.32 | 6.98 | 27.70 |
| Found | 65.16 | 6.98 | 27.52 |

Following the above procedure but substituting the optically active (+)-α-ethylbenzylamine for the racemic α-ethylbenzylamine, yields the (+)-1-cyano-3-(α-ethylbenzyl)guanidines, mp 100°–101° C.

Also, substituting the appropriate substituted aniline or amine for α-ethylbenzylamine yields the following compounds:

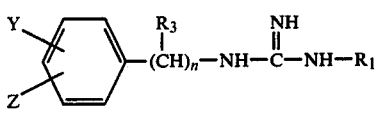

| Y | Z | R₃ | n | R₁ | mp °C. |
|---|---|---|---|---|---|
| 3-Cl | 5-Cl | — | 0 | CN | 196–198 |
| 3-OCH₃ | H | — | 1 | CN | 112–114 |
| 3-Br | H | — | 0 | CN | 236–237 |
| 3-CF₃ | H | H | 0 | CN | 203–206 |
| H | H | H | 1 | CN | 100–101 |
| 4-OH | 3-Cl | — | 0 | CN | 217–219 |
| 4-F | 3-CF₃ | — | 0 | CN | 146–148 |
| 4-F | 3-Cl | — | 0 | CN | 214.5–216 |
| H | H | C₂H₅ | 1 | CN | 121–123 |
| H | H | CH₃ | 1 | CN | 156–158 |
| 3-Cl | 5-Cl | — | 0 | NO₂ | 218–219 |
| H | H | — | 0 | NO₂ | 147–149 |
| 3-Br | 5-Br | — | 0 | NO₂ | 243-dec. |
| 3-CH₃ | 5-Br | — | 0 | NO₂ | 201–203 |
| 3-OCH₃ | 5-CF₃ | — | 0 | NO₂ | 152–154 |

EXAMPLE 3

Evaluation of Nitro- and Cyanoguanidines as Cotton Defoliants Using a Leaf-Dip Bioassay In the following tests, compounds are considered active defoliants when a single leaf abscises after being dipped in a solution of the test compound containing 5,333 ppm of test compound or less. Highly effective defoliants, such as 1-(α-ethylbenzyl)-3-nitroguanidine, will induce abscission at concentrations of 267 to 533 ppm not only of the dipped leaf but of the other leaves on the plant as well.

In the test, a solution or suspension of test compound is prepared in 6 ml of 50% aqueous/acetone. Preparation involves dispersing or dissolving 32 mg of test compound in 3.1 mL of acetone containing 0.5% v/v of a non-ionic spreader-sticker, Multifilm X-77 ®, the principal functioning agents of which are alkylarylpolyoxyethylene, glycols, free fatty acids and isopropanol, and admixing therewith 3.1 mL of deionized water. The concentration of test compound in this preparation is 5,333 ppm and equal to that of a spray solution applied at the rate of 2 kg/ha delivered in a volume of 374 liters. The thus prepared test solution is then poured into a 9 cm diameter Petri dish. Thereafter a growing, potted cotton plant is inverted and the upper surface of the 5th leaf dipped in the test solution. Care is taken to avoid contacting other parts of the plant with test solution. Excess test solution is allowed to drain from the treated leaf and thereafter the plant is placed on a bench in the greenhouse and cared for in a conventional manner. If the test compound is active, the treated leaf will abscise about 7 days post-treatment and defoliation of the entire plant may be complete in about 14 days. If a compound is active at 5333 ppm, dilutions may be made to determine the effectiveness of the compound at lower concentrations. Data obtained are reported in Table I below.

TABLE I

Leaf Dip Bioassay for Cotton Defoliation

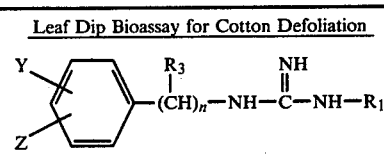

| Y | Z | R₁ | R₃ | n | Single Leaf Dip Assay ppm | Abscission |
|---|---|---|---|---|---|---|
| 3-Cl | 5-Cl | NO₂ | — | 0 | 553 | no |
|  |  |  |  |  | 2667 | yes |
|  |  |  |  |  | 5333 | yes |
| 3-Br | 5-Br | NO₂ | — | 0 | 533 | no |
|  |  |  |  |  | 2667 | yes |
|  |  |  |  |  | 5333 | yes |
| H | H | NO₂ | CH₃ | 1 | 533 | no |
|  |  |  |  |  | 5333 | yes |
| H | 2-F | NO₂ | CH₃ | 1 | 533 | yes |
|  |  |  |  |  | 5333 | yes |
| H | 4-F | NO₂ | CH₃ | 1 | 5333 | yes |
| H | H | NO₂ | C₂H₅ | 1 | 267 | yes |
|  |  |  |  |  | 533 | yes |
|  |  |  |  |  | 1067 | yes |
| H | H | NO₂ | C₂H₅(+) | 1 | 267 | yes |
|  |  |  |  |  | 533 | yes |
|  |  |  |  |  | 1067 | yes |
| H | H | NO₂ | C₂H₅(−) | 1 | 533 | yes |
|  |  |  |  |  | 5333 | yes |
| H | H | NO₂ | n-C₃H₇ | 1 | 267 | yes |
|  |  |  |  |  | 533 | yes |
|  |  |  |  |  | 2667 | yes |
|  |  |  |  |  | 5333 | yes |
| H | H | NO₂ | CH₂CH=CH₂ | 1 | 5333 | yes |
| 3-OCH₃ | H | NO₂ | CH₃ | 1 | 533 | yes |
|  |  |  |  |  | 5333 | yes |
| H | H | NO₂ | CF₃ | 1 | 5333 | yes |
| 3-OCH₃ | H | NO₂ | C₂H₅ | 1 | 533 | no |
|  |  |  |  |  | 5333 | yes |
| 3-F | H | NO₂ | C₂H₅ | 1 | 533 | yes |
|  |  |  |  |  | 5333 | yes |
| 4-F | H | NO₂ | C₂H₅ | 1 | 533 | yes |
|  |  |  |  |  | 5333 | yes |
| 2-Cl | H | NO₂ | C₂H₅ | 1 | 533 | yes |
|  |  |  |  |  | 5333 | yes |
| 4-Cl | H | NO₂ | C₂H₅ | 1 | 533 | yes |
|  |  |  |  |  | 5333 | yes |
| H | H | CN | C₂H₅ | 1 | 533 | yes |
|  |  |  |  |  | 5333 | yes |
| H | H | CN | C₂H₅(+) | 1 | 533 | no |
|  |  |  |  |  | 5333 | yes |

EXAMPLE 4

Evaluation of Test Compounds as Cotton Defoliants Applied as Foliar Sprays

In the following tests cotton plants having 12 to 14 leaves are sprayed with 50/50 aqueous/acetone mixtures containing sufficient test compound to provide from 0.10 to 2.0 kg/ha of test compound when sprayed to run-off with the test solution or suspension. The test solutions also contain 0.25% V/V of a non-ionic surfactant or spreader-sticker, the principal functioning agents of which are alkylarylpolyoxyethylene, glycols, free fatty acids and isopropanol. Each test is replicated four times and the treated plants are then placed on greenhouse benches and examined at intervals during the 14 days post treatment. Data obtained are reported in Table II below as % defoliation.

TABLE II

Cotton Defoliation Using Foliar Spray of Test Compound

| Y | Z | R₁ | R₃ | n | Rate kg/ha | % Defoliation |
|---|---|----|----|----|-----------|---------------|
| 3-Cl | 5-Cl | NO₂ | — | 0 | 0.23 | 53 |
|  |  |  |  |  | 0.68 | 71 |
|  |  |  |  |  | 1.35 | 95 |
| H | H | NO₂ | CH₃ | 1 | 0.2 | 60 |
|  |  |  |  |  | 2.0 | 60 |
| H | H | NO₂ | CH₃(+) | 1 | 0.06 | 59 |
|  |  |  |  |  | 0.12 | 66 |
|  |  |  |  |  | 0.18 | 79 |
| H | 2-F | NO₂ | CH₃ | 1 | 0.2 | 39 |
|  |  |  |  |  | 2.0 | 54 |
| H | 3-F | NO₂ | CH₃ | 1 | 0.1 | 50 |
|  |  |  |  |  | 0.2 | 63 |
|  |  |  |  |  | 0.4 | 55 |
| H | 4-F | NO₂ | CH₃ | 1 | 2.0 | 58 |
| H | H | NO₂ | C₂H₅ | 1 | 0.1 | 71 |
|  |  |  |  |  | 0.2 | 86 |
|  |  |  |  |  | 0.4 | 89 |
| H | H | NO₂ | C₂H₅(+) | 1 | 0.1 | 100 |
|  |  |  |  |  | 0.2 | 100 |
|  |  |  |  |  | 0.4 | 100 |
| H | H | NO₂ | C₂H₅(−) | 1 | 0.2 | 71 |
|  |  |  |  |  | 2.0 | 86 |
| H | H | NO₂ | CF₃ | 1 | 2.0 | 69 |
| H | H | CN | C₂H₅ | 1 | 0.2 | 50 |
|  |  |  |  |  | 2.0 | 88 |

EXAMPLE 5

Evaluation of 1-(α-Ethylbenzyl)-3-Nitroguanidine as a Defoliant for Cotton (Variety: Deltapine 41)

In the following field evaluation cotton plants (variety: Deltapine 41) growing in late bloom stage with at least 60% of the bolls open, are sprayed with an aqueous suspension of 1-(α-ethylbenzyl)-3-nitroguanidine. The test composition is prepared by admixing 69.25% by weight of water with 0.15% by weight of xanthan gum; 0.3% by weight of nonylphenoxy polyethoxy ethanol (Triton N101 ® marketed by Rohm and Haas Co.); 3.0% by weight of an ammonium salt of a condensed mononaphthalene sulfonic acid (Lomar PWA marketed by Diamond Shamrock; 0.1% by weight of paraformaldehyde; 0.2% by weight of a 30% mixture of dimethylpolysiloxane (Magu DF243 marketed by Mazer Chemicals Inc.) and 21% by weight of 1-(α-ethylbenzyl)-3-nitroguanidine.

This composition is then dispersed in water in a sufficient amount to provide from 0.038 kg/ha to 0.6 kg/ha of active ingredient when the aqueous suspension is sprayed on the cotton plants at the rate of 31 gallons per hectare. Three replications per treatment are employed. Ten days after treatments are made the plants are examined and the percent defoliation recorded. Data obtained are reported in Table III below.

TABLE III

Evaluation of 1-(α-ethylbenzyl)-3-nitroguanidine for defoliation of cotton (variety: Deltapine 41)

| Compound | Rate kg/ha | % Defoliation |
|----------|-----------|---------------|
| Untreated Control | 0 | 0 |
| 1-(α-ethylbenzyl)-3-nitroguanidine | 0.038 | 60 |
|  | 0.075 | 70 |
|  | 0.15 | 80 |
|  | 0.3 | 95 |
|  | 0.6 | 95 |

EXAMPLE 6

Preemergence Herbicidal Evaluation of Test Compounds

The preemergence herbicidal activity of the compounds of the present invention is exemplified by the following tests in which the seeds of a variety of monocotyledonous and dicotyledonous plants are separately mixed with potting soil and planted on top of approximately one inch of soil in separate pint cups. After planting, the cups are sprayed with the selected aqueous acetone solution containing test compound in sufficient quantity to provide the equivalent of about 1.0 kg to 8.0 kg per hectare of test compound per cup. The treated cups are then placed on greenhouse benches, watered and cared for in accordance with conventional greenhouse procedures. From four to five weeks after treatment, the tests are terminated and each cup is examined and rated according to the rating system set forth below. The herbicidal proficiency of the active ingredients of the present invention is evident from the test results which are recorded in Tables, IV to XVIII below. Where more than one test is involved for a given compound, the data are averaged.

Preparation of the test compositions are as follows:

The test compounds are dispersed in 50/50 acetone/water mixtures containing 0.5% TWEEN ® 20, a polyoxyethylene sorbitan monolaurate surfactant of Atlas Chemical Industries, in sufficient quantity to provide the equivalent of about 1.0 kg to 8.0 kg per hectare of active compound when applied to the plants through a spray nozzle operating at 40 psi for a predetermined time. Results of herbicide evaluation are expressed on a rating scale (0–9). The scale is based upon a visual observation of plant stand, vigor, malformation, size, chlorosis and overall plant appearance as compared with a control.

| Rating | Meaning | % control (compared to check) |
|--------|---------|-------------------------------|
| 9 | Complete kill | 100 |
| 8 | Approaching complete kill | 91–99 |
| 7 | Good herbicidal effect | 80–90 |
| 6 | Herbicidal effect | 65–79 |
| 5 | Definite injury | 45–64 |
| 4 | Injury | 30–44 |
| 3 | Moderate effect | 16–29 |
| 2 | Slight effect | 6–15 |
| 1 | Trace effect | 1–5 |
| 0 | No effect | 0 |

Plant Species Employed in the Following Tests

| Common name | Scientific name |
|-------------|-----------------|
| Barnyardgrass | *Echinochloa crus-galli*, (L) Beau |
| Bermudagrass | *Cynodon dactylon*, (L) Pers. |
| Blackgrass | *Alopecurus myosuroides* |

| Common name | Scientific name |
|---|---|
| Brome, Downy | Bromus tectorum, L. |
| Canarygrass, Littleseed | Phalaris minor, Retz. |
| Cogongrass | Imperata cylindrica, (L) Beauv. |
| Crabgrass, (Hairy) large | Digitaria sanguinalis, (L) Scop |
| Foxtail, Green | Setaria viridis, (L) Beauv |
| Itchgrass | Rottboellia exaltata L. |
| Goosegrass | Eleusine indica, (L) Gaertn |
| Johnsongrass (from Rhizomes) | Sorghum halepense (Rhizomes) |
| Nutsedge, Purple | Cyperus rotundus, L. |
| Oat, Wild | Avena fatua, L. |
| Lolium | Lolium perenne, L. |
| Quackgrass | Agropyron repens, (L) Beauv. |
| Beggartick (Spanishneedles) | Bidens, spp. |
| Bindweed, Field (Rhizome) | Convolvulus arvensis, L. |
| Cocklebur | Xanthium Pensylvanicum, Wallr. |
| Nightshade, Red | Solanum dulcamara |
| Horsenettle | Solanum carolinense, L. |
| Lambsquarters, Common | Chenopodium album, L. |
| Matricaria, spp. | Matricaria, spp. |
| Milkweed, Common | Asclepias syriaca, L. |
| Morningglory, Spp. | Ipomoea, spp. |
| Mustard, Wild | Brassica kaber, (DC) L.C. Wheelr |
| Pigweed, Redroot | Amaranthus retroflexus, L. |
| Ragweed, Common | Ambrosia artemisiifolia, L. |
| Sida, Prickly | Sida spinosa, L. |
| Smartweed, Pennsylvania | Polygonum Pensylvanicum, L. |
| Thistle, Canada (Rhizome) | Cirsium arvense, (L) Scop. |
| Velvetleaf | Abutilon theophrasti, Medic. |
| Euphorbia Heterophylla | Euphorbia heterophylla, L. |
| Bulrush | Scirpus, spp. |
| Parrotfeather | Myriophyllum brasiliense, Camb. |
| Wheat, Winter, Fenman | Triticum aestivum, CV Fenman |
| Barley, Spring, Larker | Hordeum vulgare, CV. Larker |
| Sugarbeets | Beta vulgaris, L. |
| Corn, Field | Zea mays, L. |
| Cotton | Gossypium hirsutum, L. |
| Millet, Foxtail, Cultivated | Setaria italica |
| Radish | Raphanus sativus, L. |
| Rice, Nato | Oryza sativa, L. CV. Nato |
| Sorghum, Grain | Sorghum bicolor, (L) Moench |

TABLE IV

Preemergence herbicidal evaluation of test compounds

| Compound | Plant Species | 8.0 | 4.0 | 2.0 | 1.0 |
|---|---|---|---|---|---|
| 1-[α-(Methoxy-methyl)benzyl]-3-nitroguanidine | BARNYARDGRASS | 6.0 | | | |
| | BERMUDAGRASS | | | 1.0 | 1.0 |
| | COGONGRASS | | | 0.0 | 0.0 |
| | CRABGRASS,(HAIRY) L | | 1.0 | | |
| | FOXTAIL,GREEN | 8.0 | | | |
| | JOHNSONGRASS (FROM R) | | | 6.0 | 2.0 |
| | NUTSEDGE,PURPLE | 7.0 | | | |
| | QUACKGRASS | 9.0 | | | |
| | BEGGARTICK (SPANISHN) | | | 9.0 | 9.0 |
| | BINDWEED,FIELD (RHIZ) | 8.0 | 9.0 | | 8.0 |
| | COCKLEBUR | | | 9.0 | 7.0 |
| | NIGHTSHADE,RED | | | 9.0 | 9.0 |
| | HORSENETTLE | | | 9.0 | 9.0 |
| | MATRICARIA SPP. | | | 9.0 | 8.0 |
| | MILKWEED,COMMON | | | 9.0 | 8.0 |
| | MORNINGGLORY SPP. | 9.0 | 8.0 | | 7.0 |
| | MUSTARD,WILD | 8.0 | 8.0 | 8.0 | |
| | PIGWEED,REDROOT | | | 9.0 | 9.0 |
| | RAGWEED,COMMON | 8.0 | 9.0 | | 9.0 |
| | SIDA,PRICKLY | 9.0 | 9.0 | | 9.0 |
| | SMARTWEED,PENNSYLVA | | | 7.0 | 4.0 |
| | THISTLE,CANADA (RHIZ) | | | 9.0 | 9.0 |
| | VELVETLEAF | 9.0 | 9.0 | | 9.0 |
| | EUPHORBIA HETEROPHYL | | | 9.0 | 6.0 |
| | SUGARBEETS | | | 7.5 | 7.0 |
| | CORN,FIELD | | | 5.0 | 0.0 |
| | COTTON | | | 9.0 | 9.0 |
| | RICE,NATO | | | 5.5 | 3.0 |
| | SOYBEAN,ADELPHIA | | | 8.5 | 7.0 |
| | SUNFLOWER,UNSPECIFIE | | | 9.0 | 6.0 |

TABLE V

Preemergence herbicidal evaluation of test compounds

| Compound | Plant Species | 8.0 | 4.0 | 2.0 | 1.0 |
|---|---|---|---|---|---|
| 1-[α-Allylbenzyl)-3-nitroguanidine | BARNYARDGRASS | 8.0 | 7.0 | | 2.0 |
| | BERMUDAGRASS | | 4.0 | | 0.0 |
| | BLACKGRASS | | 6.0 | | 2.0 |
| | BROME,DOWNY | | 7.0 | | 3.0 |
| | CANARYGRASS,LITTLES | | 7.0 | | 3.0 |
| | COGONGRASS | | 7.0 | | 0.0 |
| | CRABGRASS,(HAIRY) L | 8.0 | 3.0 | | 2.0 |
| | FOXTAIL,GREEN | 9.0 | 7.0 | | 5.0 |
| | ITCHGRASS | | 7.0 | | 2.0 |
| | GOOSEGRASS | | 2.0 | | 0.0 |
| | JOHNSONGRASS (FROM R) | | 5.0 | | 3.0 |
| | NUTSEDGE,PURPLE | 6.0 | 6.0 | | 4.0 |
| | OAT,WILD | 3.0 | 0.0 | | 0.0 |
| | LOLIUM | | 4.0 | | 0.0 |
| | PANICUM,FALL | | 7.0 | | 6.0 |
| | QUACKGRASS | 9.0 | 9.0 | | 4.0 |
| | BEGGARTICK (SPANISHN) | | 9.0 | | 9.0 |
| | BINDWEED,FIELD (RHIZ) | 9.0 | 9.0 | | 6.0 |
| | COCKLEBUR | | 9.0 | | 9.0 |
| | NIGHTSHADE,RED | | 9.0 | | 9.0 |
| | HORSENETTLE | | 9.0 | | 9.0 |
| | MATRICARIA SPP. | | 9.0 | | 9.0 |
| | MILKWEED,COMMON | | 9.0 | | 9.0 |
| | MORNINGGLORY SPP. | 9.0 | 8.0 | | 8.0 |
| | MUSTARD,WILD | 9.0 | 9.0 | | 9.0 |
| | PIGWEED,REDROOT | | 9.0 | | 9.0 |
| | RAGWEED,COMMON | 8.0 | 7.0 | | 5.0 |
| | SIDA,PRICKLY | 9.0 | 9.0 | | 9.0 |
| | SMARTWEED,PENNSYLVA | | 8.0 | | 8.0 |
| | THISTLE,CANADA (RHIZ) | | 9.0 | | 9.0 |
| | VELVETLEAF | 9.0 | 9.0 | | 9.0 |
| | EUPHORBIA HETEROPHYL | | 9.0 | | 7.0 |
| | BULRUSH | | 4.0 | | 3.0 |
| | WHEAT,WINTER,FENMA | | 5.3 | | 2.3 |

TABLE VI

Preemergence herbicidal evaluation of test compounds

| Compound | Plant Species | 8.0 | 4.0 | 2.0 | 1.0 |
|---|---|---|---|---|---|
| (+)-1-(α-Ethylbenzyl)-3-nitroguanidine | BARNYARDGRASS | 9.0 | 8.0 | | 6.0 |
| | BLACKGRASSS | | 8.0 | | 4.0 |
| | BROME,DOWNY | | 8.0 | | 4.0 |
| | CANARYGRASS,LITTLES | | 9.0 | | 7.0 |
| | CRABGRASS,(HAIRY) L | 9.0 | 8.0 | | 6.0 |
| | FOXTAIL,GREEN | 8.0 | 8.0 | | 4.0 |
| | ITCHGRASS | | 9.0 | | 6.0 |
| | GOOSEGRASS | | 8.0 | | 4.0 |
| | NUTSEDGE,PURPLE | 8.0 | | 7.0 | 6.0 |
| | OAT,WILD | 8.0 | 3.0 | | 2.0 |
| | LOLIUM | | 7.0 | | 5.0 |
| | PANICUM,FALL | | 9.0 | | 4.0 |
| | QUACKGRASS | 9.0 | | 6.0 | 5.0 |
| | BINDWEED,FIELD (RHIZ) | 9.0 | | 9.0 | 9.0 |
| | COCKLEBUR | | 9.0 | 9.0 | 8.0 |
| | LAMBSQUARTERS,COMMO | | | 9.0 | 8.0 |
| | MATRICARIA SPP. | | 8.0 | | 9.0 |
| | MORNINGGLORY SPP. | 9.0 | 9.0 | 7.0 | 7.5 |
| | MUSTARD,WILD | 9.0 | 8.0 | 9.0 | 8.0 |
| | PIGWEED,REDROOT | | 9.0 | 9.0 | 9.0 |
| | RAGWEED,COMMON | 8.0 | 7.0 | 7.0 | 5.5 |
| | SIDA,PRICKLY | 9.0 | 9.0 | | 9.0 |
| | SMARTWEED,PENNSYLVA | | 8.0 | 6.0 | 5.0 |
| | VELVETLEAF | 9.0 | 9.0 | 8.0 | 8.5 |
| | EUPHORBIA HETEROPHYL | | 9.0 | | 9.0 |

TABLE VI-continued

Preemergence herbicidal evaluation of test compounds

| Compound | Plant Species | Rates in kg/ha | | | |
|---|---|---|---|---|---|
| | | 8.0 | 4.0 | 2.0 | 1.0 |
| | WHEAT,WINTER,FENMA | | | 2.0 | 0.0 |
| | BARLEY,SPRING,LARKER | | | 2.0 | 0.0 |
| | SUGARBEETS | | | 9.0 | 9.0 |
| | CORN,FIELD | | 3.0 | 1.0 | 1.0 |
| | COTTON | | | 9.0 | 9.0 |
| | RICE,NATO | 8.0 | 4.0 | | 3.3 |
| | SORGHUM,GRAIN | | | 0.0 | 0.0 |
| | SOYBEAN,ADELPHIA | | | 9.0 | 9.0 |
| | SUNFLOWER,UNSPECIFIE | | | 9.0 | 6.5 |
| | WHEAT,SPRING,ERA | | | 2.0 | 2.5 |

TABLE VII

Preemergence herbicidal evaluation of test compounds

| Compound | Plant Species | Rates in kg/ha | | | |
|---|---|---|---|---|---|
| | | 8.0 | 4.0 | 2.0 | 1.0 |
| 1-Nitro-3-(α-propylbenzyl)-guanidine | BARNYARDGRASS | 6.0 | 0.0 | | 0.0 |
| | BERMUDAGRASS | | 5.0 | | 0.0 |
| | BLACKGRASS | | 4.0 | | 0.0 |
| | BROME,DOWNY | | 3.0 | | 0.0 |
| | CANARYGRASS,LITTLES | | 0.0 | | 0.0 |
| | COGONGRASS | | 0.0 | | 0.0 |
| | CRABGRASS,(HAIRY) L | 2.0 | 0.0 | | 0.0 |
| | FOXTAIL,GREEN | 8.0 | 7.0 | | 0.0 |
| | ITCHGRASS | | 9.0 | | 0.0 |
| | GOOSEGRASS | | 0.0 | | 0.0 |
| | JOHNSONGRASS (FROM R) | | | | 0.0 |
| | NUTSEDGE,PURPLE | 6.0 | | 5.0 | 4.0 |
| | OAT,WILD | 0.0 | 3.0 | | 0.0 |
| | LOLIUM | | 0.0 | | 0.0 |
| | PANICUM,FALL | | 7.0 | | 0.0 |
| | QUACKGRASS | 9.0 | 3.0 | 4.0 | 0.0 |
| | BINDWEED,FIELD (RHIZ) | 9.0 | 8.0 | 9.0 | 2.5 |
| | COCKLEBUR | | | 8.0 | 7.0 |
| | NIGHTSHADE,RED | | | 2.0 | |
| | HORSENETTLE | | 9.0 | | 6.0 |
| | LAMBSQUARTERS,COMMO | | | 6.0 | 3.0 |
| | MILKWEED,COMMON | | 9.0 | | |
| | MORNINGGLORY SPP. | 6.0 | | 2.0 | 0.0 |
| | MUSTARD,WILD | 8.0 | | 8.0 | 4.0 |
| | PIGWEED,REDROOT | | | 8.0 | 7.0 |
| | RAGWEED,COMMON | 9.0 | | 7.0 | 4.0 |
| | SIDA,PRICKLY | 9.0 | | | |
| | SMARTWEED PENNSYLVA | | | 0.0 | 0.0 |
| | THISTLE,CANADA (RHIZ) | | 9.0 | | 9.0 |
| | VELVETLEAF | 9.0 | | 9.0 | 9.0 |
| | BULRUSH | | | | 0.0 |
| | WHEAT,WINTER,FENMA | | 3.0 | 0.0 | 0.0 |
| | BARLEY,SPRING,LARKER | | | 0.0 | 0.0 |
| | SUGARBEETS | | 7.0 | | 6.0 |
| | CORN,FIELD | 0.0 | 0.0 | | 0.0 |
| | COTTON | | 9.0 | | 9.0 |
| | RICE,NATO | 4.0 | 0.0 | | 0.7 |
| | SORHGUM,GRAIN | | | 0.0 | 0.0 |
| | SOYBEAN,ADELPHIA | | 5.0 | | 3.0 |
| | SUNFLOWER,UNSPECIFIE | | 8.5 | | 3.5 |

TABLE VIII

Preemergence herbicidal evaluation of test compounds

| Compound | Plant Species | Rates in kg/ha | | | |
|---|---|---|---|---|---|
| | | 8.0 | 4.0 | 2.0 | 1.0 |
| 1-(α-Ethylbenzyl)-3-nitroguanidine | BARNYARDGRASS | 9.0 | 7.0 | | 6.0 |
| | BERMUDAGRASS | | 9.0 | | 3.0 |
| | BLACKGRASS | | 7.0 | | 7.0 |
| | BROME,DOWNY | | 3.0 | | 3.0 |
| | CANARYGRASS,LITTLES | | 9.0 | | 7.0 |
| | COGONGRASS | | | | 6.0 |
| | CRABGRASS,(HAIRY) L | 9.0 | 9.0 | | 3.0 |
| | FOXTAIL,GREEN | 9.0 | 7.0 | | 3.0 |
| | ITCHGRASS | | 9.0 | | 4.0 |
| | GOOSEGRASS | | 7.0 | | 3.0 |
| | JOHNSONGRASS (FROM R) | | | | 0.0 |
| | NUTSEDGE,PURPLE | 9.0 | 8.0 | 9.0 | 4.0 |
| | OAT,WILD | 4.0 | 4.0 | | 3.0 |
| | LOLIUM | | 4.0 | | 3.0 |
| | PANICUM,FALL | | 7.0 | | 5.0 |
| | QUACKGRASS | 9.0 | 7.0 | 2.0 | 1.0 |
| | BINDWEED,FIELD (RHIZ) | 9.0 | 9.0 | 9.0 | 8.5 |
| | COCKLEBUR | | | 9.0 | 6.0 |
| | NIGHTSHADE,RED | | 9.0 | | 9.0 |
| | HORSENETTLE | | 9.0 | | 9.0 |
| | LAMBSQUARTERS,COMMO | | | 7.0 | 6.0 |
| | MILKWEED,COMMON | | 9.0 | | 9.0 |
| | MORNINGGLORY SPP. | 9.0 | | 8.0 | 4.0 |
| | MUSTARD,WILD | 9.0 | | 9.0 | 9.0 |
| | PIGWEED,REDROOT | | | 9.0 | 9.0 |
| | RAGWEED,COMMON | 8.0 | | 7.0 | 3.0 |
| | SIDA,PRICKLY | 9.0 | | | |
| | SMARTWEED PENNSYLVA | | | 3.0 | 0.0 |
| | THISTLE,CANADA (RHIZ) | | 9.0 | | 9.0 |
| | VELVETLEAF | 9.0 | | 9.0 | 5.0 |
| | WHEAT,WINTER,FENMA | | 3.0 | 0.0 | 1.5 |
| | BARLEY,SPRING,LARKER | | | 0.0 | 0.0 |
| | SUGARBEETS | | 9.0 | | 7.0 |
| | CORN,FIELD | 0.0 | 0.0 | | 0.0 |
| | COTTON | | 9.0 | | 9.0 |
| | RICE,NATO | 6.0 | 0.0 | | 1.5 |
| | SORHGUM,GRAIN | | | 1.0 | 1.0 |
| | SOYBEAN,ADELPHIA | | 9.0 | | 7.0 |
| | SUNFLOWER,UNSPECIFIE | | 9.0 | | 5.0 |

TABLE IX

Preemergence herbicidal evaluation of test compounds

| Compound | Plant Species | Rates in kg/ha | | | |
|---|---|---|---|---|---|
| | | 8.0 | 4.0 | 2.0 | 1.0 |
| (+)-1-(α-Methylbenzyl)-3-nitro-guanidine | BARNYARDGRASS | 8.0 | 8.0 | | 5.0 |
| | BLACKGRASSS | | 8.0 | | 3.0 |
| | BROME,DOWNY | | 6.0 | | 0.0 |
| | CANARYGRASS,LITTLES | | 9.0 | | 4.0 |
| | CRABGRASS,(HAIRY) L | 9.0 | 8.0 | | 4.0 |
| | FOXTAIL,GREEN | 8.0 | 2.0 | | 2.0 |
| | ITCHGRASS | | 7.0 | | 0.0 |
| | GOOSEGRASS | | 6.0 | | 2.0 |
| | NUTSEDGE,PURPLE | 8.0 | | | |
| | OAT,WILD | 8.0 | 2.0 | | 1.0 |
| | LOLIUM | | 8.0 | | 4.0 |
| | PANICUM,FALL | | 9.0 | | 2.0 |
| | QUACKGRASS | 5.0 | | | |
| | BINDWEED,FIELD (RHIZ) | 9.0 | | | |
| | COCKLEBUR | | 8.0 | | 3.0 |
| | MATRICARIA SPP. | | 7.0 | | 5.0 |
| | MORNINGGLORY SPP. | 8.0 | 8.0 | | 6.0 |
| | MUSTARD,WILD | 9.0 | 7.0 | | 3.0 |
| | PIGWEED,REDROOT | | 8.0 | | 6.0 |
| | RAGWEED,COMMON | 9.0 | 6.0 | | 0.0 |
| | SIDA,PRICKLY | 9.0 | 9.0 | | 4.0 |
| | SMARTWEED,PENNSYLVA | | 7.0 | | 4.0 |
| | VELVETLEAF | 9.0 | 9.0 | | 6.0 |
| | *EUPHORBIA HETEROPHYL* | | 7.0 | | 3.0 |
| | SUGARBEETS | | 8.0 | | 6.5 |
| | CORN,FIELD | | 1.0 | | 0.0 |
| | COTTON | | 9.0 | | 9.0 |
| | RICE,NATO | | 4.0 | | 1.5 |
| | SOYBEAN,ADELPHIA | | 9.0 | | 7.5 |
| | SUNFLOWER,UNSPECIFIE | | 8.5 | | 1.0 |
| | WHEAT,SPRING,ERA | | 1.5 | | 0.5 |

TABLE X

Preemergence herbicidal evaluation of test compounds

| Compound | Plant Species | Rates in kg/ha | | | |
|---|---|---|---|---|---|
| | | 8.0 | 4.0 | 2.0 | 1.0 |
| 1-(α-Ethyl-m-fluorobenzyl)-3-nitroguanidine | BARNYARDGRASS | 9.0 | 9.0 | | 4.0 |
| | BERMUDAGRASS | | 7.0 | | 2.0 |
| | BLACKGRASS | | 8.0 | | 3.0 |
| | BROME,DOWNY | | 7.0 | | 3.0 |

TABLE X-continued

Preemergence herbicidal evaluation of test compounds

| Compound | Plant Species | 8.0 | 4.0 | 2.0 | 1.0 |
|---|---|---|---|---|---|
| | CANARYGRASS,LITTLES | | | 9.0 | 7.0 |
| | COGONGRASS | | | 0.0 | 0.0 |
| | CRABGRASS,(HAIRY) L | 9.0 | 9.0 | | 4.0 |
| | FOXTAIL,GREEN | 9.0 | 9.0 | | 4.0 |
| | ITCHGRASS | | | 8.0 | 3.0 |
| | GOOSEGRASS | | | 7.0 | 3.0 |
| | JOHNSONGRASS (FROM R) | | | 7.0 | 1.0 |
| | NUTSEDGE,PURPLE | 7.0 | 6.0 | | 5.0 |
| | OAT,WILD | 7.0 | 7.0 | | 3.0 |
| | LOLIUM | | | 8.0 | 3.0 |
| | PANICUM,FALL | | | 8.0 | 3.0 |
| | QUACKGRASS | 9.0 | 5.0 | | 0.0 |
| | BEGGARTICK SPANISHN | | | 8.0 | 7.0 |
| | BINDWEED,FIELD (RHIZ) | 9.0 | 8.0 | | 8.0 |
| | COCKLEBUR | | | 9.0 | 9.0 |
| | NIGHTSHADE,RED | | | 9.0 | 7.0 |
| | HORSENETTLE | | | 9.0 | 6.0 |
| | MATRICARIA SPP. | | | 9.0 | 8.0 |
| | MILKWEED,COMMON | | | 9.0 | 7.0 |
| | MORNINGGLORY SPP. | 9.0 | 7.0 | | 6.0 |
| | MUSTARD,WILD | 9.0 | 9.0 | | 9.0 |
| | PIGWEED,REDROOT | | | 9.0 | 9.0 |
| | RAGWEED,COMMON | 8.0 | 7.0 | | 5.0 |
| | SIDA,PRICKLY | 9.0 | 9.0 | | 9.0 |
| | SMARTWEED,PENNSYLVA | | | 7.0 | 4.0 |
| | THISTLE,CANADA (RHIZ) | | | 9.0 | 9.0 |
| | VELVETLEAF | 9.0 | 9.0 | | 7.0 |
| | *EUPHORBIA HETEROPHYL* | | | 9.0 | 6.0 |
| | BULRUSH | | | 3.0 | 1.0 |
| | WHEAT,WINTER,FENMA | | | 4.3 | 1.7 |
| | SUGARBEETS | | | 8.3 | 6.3 |
| | CORN,FIELD | | | 2.0 | 0.0 |
| | COTTON | | | 9.0 | 9.0 |
| | RICE,NATO | | | 6.3 | 2.3 |
| | SOYBEAN,ADELPHIA | | | 9.0 | 6.3 |
| | SUNFLOWER,UNSPECIFIE | | | 9.0 | 7.3 |

TABLE XI

Preemergence herbicidal evaluation of test compounds

| Compound | Plant Species | 8.0 | 4.0 | 2.0 | 1.0 |
|---|---|---|---|---|---|
| 1-(α-Ethyl-m- | BARNYARDGRASS | 9.0 | 4.0 | | 0.0 |
| methoxybenzyl)- | BERMUDAGRASS | | | 9.0 | 4.0 |
| 3-nitroguanidine | BLACKGRASS | | | 3.0 | 0.0 |
| | BROME,DOWNY | | | 0.0 | 0.0 |
| | CANARYGRASS,LITTLES | | | 8.0 | 0.0 |
| | COGONGRASS | | | | 6.0 |
| | CRABGRASS,(HAIRY) L | 9.0 | 3.0 | | 0.0 |
| | FOXTAIL,GREEN | 8.0 | 0.0 | | 0.0 |
| | ITCHGRASS | | | 0.0 | 0.0 |
| | GOOSEGRASS | | | 2.0 | 0.0 |
| | JOHNSONGRASS (FROM R) | | | 0.0 | 0.0 |
| | NUTSEDGE,PURPLE | 6.0 | | 9.0 | 5.0 |
| | OAT,WILD | 4.0 | 3.0 | | 0.0 |
| | LOLIUM | | | 0.0 | 0.0 |
| | PANICUM,FALL | | | 0.0 | 0.0 |
| | QUACKGRASS | 0.0 | 0.0 | 7.0 | 0.0 |
| | BINDWEED,FIELD (RHIZ) | 9.0 | 9.0 | 8.0 | 4.5 |
| | COCKLEBUR | | | 0.0 | 0.0 |
| | NIGHTSHADE,RED | | | 6.0 | 4.0 |
| | HORSENETTLE | | | 9.0 | 9.0 |
| | LAMBSQUARTERS,COMMO | | | 7.0 | 0.0 |
| | MILKWEED,COMMON | | | 9.0 | 9.0 |
| | MORNINGGLORY SPP. | 7.0 | | 7.0 | 0.0 |
| | MUSTARD,WILD | 8.0 | | 8.0 | 7.0 |
| | PIGWEED,REDROOT | | | 9.0 | 8.0 |
| | RAGWEED,COMMON | 7.0 | | 3.0 | 0.0 |
| | SIDA,PRICKLY | 9.0 | | | |
| | SMARTWEED,PENNSYLVA | | | 0.0 | 0.0 |
| | THISTLE,CANADA (RHIZ) | | 9.0 | | 9.0 |
| | VELVETLEAF | 8.0 | | 7.0 | 0.0 |
| | BULRUSH | | | | 3.0 |
| | WHEAT,WINTER,FENMA | | 3.0 | 0.0 | 1.0 |
| | BARLEY,SPRING,LARKER | | | 0.0 | 0.0 |
| | SUGARBEETS | | | 8.0 | 4.5 |

TABLE XI-continued

Preemergence herbicidal evaluation of test compounds

| Compound | Plant Species | 8.0 | 4.0 | 2.0 | 1.0 |
|---|---|---|---|---|---|
| | CORN,FIELD | | 2.0 | 0.0 | 0.3 |
| | COTTON | | | 6.0 | 3.0 |
| | RICE,NATO | | 1.0 | 3.0 | 0.5 |
| | SORGHUM,GRAIN | | | 2.0 | 0.0 |
| | SOYBEAN,ADELPHIA | | | 6.0 | 3.0 |
| | SUNFLOWER,UNSPECIFIE | | | 6.0 | 1.5 |

TABLE XII

Preemergence herbicidal evaluation of test compounds

| Compound | Plant Species | 8.0 | 4.0 | 2.0 | 1.0 |
|---|---|---|---|---|---|
| 1-Cyano-3- | BARNYARDGRASS | 8.0 | 8.0 | | 2.0 |
| (α-ethylbenzyl)- | BLACKGRASS | | | 7.0 | 0.0 |
| guanidine | BROME,DOWNY | | | 5.0 | 0.0 |
| | CANARYGRASS,LITTLES | | | 9.0 | 3.0 |
| | CRABGRASS,(HAIRY) L | 9.0 | 8.0 | | 0.0 |
| | FOXTAIL,GREEN | 9.0 | 8.0 | | 0.0 |
| | ITCHGRASS | | | 3.0 | 0.0 |
| | GOOSEGRASS | | | 3.0 | 0.0 |
| | NUTSEDGE,PURPLE | | 7.0 | | |
| | OAT,WILD | | 5.0 | 2.0 | 0.0 |
| | LOLIUM | | | 7.0 | 0.0 |
| | PANICUM,FALL | | | 4.0 | 0.0 |
| | QUACKGRASS | | 1.0 | | |
| | BINDWEED,FIELD (RHIZ) | | 9.0 | | |
| | COCKLEBUR | | | 9.0 | 5.0 |
| | MATRICARIA SPP. | | | 9.0 | 7.0 |
| | MORNINGGLORY SPP. | 6.0 | 6.0 | | 3.0 |
| | MUSTARD,WILD | 8.0 | 7.0 | | 6.0 |
| | PIGWEED,REDROOT | | | 9.0 | 9.0 |
| | RAGWEED,COMMON | 9.0 | 6.0 | | 3.0 |
| | SIDA,PRICKLY | 9.0 | 9.0 | | 9.0 |
| | SMARTWEED,PENNSYLVA | | | 7.0 | 2.0 |
| | VELVETLEAF | 9.0 | 9.0 | | 6.0 |
| | *EUPHORBIA HETEROPHYL* | | | 9.0 | 6.0 |
| | SUGARBEETS | | | 8.0 | 6.0 |
| | CORN,FIELD | | | 0.0 | 0.0 |
| | COTTON | | | 9.0 | 6.5 |
| | RICE,NATO | | | 4.5 | 2.5 |
| | SOYBEAN,ADELPHIA | | | 7.0 | 6.5 |
| | SUNFLOWER,UNSPECIFIE | | | 6.5 | 1.5 |
| | WHEAT,SPRING,ERA | | | 2.0 | 0.0 |

TABLE XIII

Preemergence herbicidal evaluation of test compounds

| Compound | Plant Species | 8.0 | 4.0 | 2.0 | 1.0 |
|---|---|---|---|---|---|
| 1-(α- | BARNYARDGRASS | 9.0 | 7.0 | | 2.0 |
| Methylbenzyl- | BERMUDAGRASS | | | 9.0 | 0.0 |
| 3-nitroguanidine | BLACKGRASS | | | 6.0 | 2.0 |
| | BROME,DOWNY | | | 7.0 | 3.0 |
| | CANARYGRASS,LITTLES | | | 6.0 | 4.0 |
| | CRABGRASS,(HAIRY) L | 9.0 | 7.0 | | 2.0 |
| | FOXTAIL,GREEN | 6.0 | 3.0 | | 0.0 |
| | ITCHGRASS | | | 6.0 | 3.0 |
| | GOOSEGRASS | | | 6.0 | 3.0 |
| | JOHNSONGRASS (FROM R) | | | 0.0 | 0.0 |
| | NUTSEDGE,PURPLE | 5.0 | 2.0 | | 0.0 |
| | OAT,WILD | 5.0 | 6.0 | | 2.0 |
| | LOLIUM | | | 6.0 | 2.0 |
| | PANICUM,FALL | | | 6.0 | 2.0 |
| | QUACKGRASS | 5.0 | 0.0 | | 0.0 |
| | BEGGARTICK (SPANISHN) | | | 9.0 | 3.0 |
| | BINDWEED,FIELD (RHIZ) | 9.0 | 9.0 | | 4.0 |
| | COCKLEBUR | | | 7.0 | 1.0 |
| | NIGHTSHADE,RED | | | 9.0 | 4.0 |
| | HORSENETTLE | | | 8.0 | 3.0 |
| | MATRICARIA SPP. | | | 7.0 | 2.0 |
| | MORNINGGLORY SPP. | 6.0 | 6.0 | | 2.0 |
| | MUSTARD,WILD | 9.0 | 6.0 | | 2.0 |
| | PIGWEED,REDROOT | | | 6.0 | 1.0 |
| | RAGWEED,COMMON | 9.0 | 7.0 | | 1.0 |

TABLE XIII-continued

Preemergence herbicidal evaluation of test compounds

| Compound | Plant Species | Rates in kg/ha | | | |
|---|---|---|---|---|---|
| | | 8.0 | 4.0 | 2.0 | 1.0 |
| | SIDA,PRICKLY | | 7.0 | 9.0 | 3.0 |
| | SMARTWEED,PENNSYLVA | | | 6.0 | 2.0 |
| | THISTLE,CANADA (RHIZ) | | | 9.0 | 9.0 |
| | VELVETLEAF | 9.0 | 8.0 | 8.0 | 4.0 |
| | *EUPHORBIA HETEROPHYL* | | | 7.0 | 4.0 |
| | BULRUSH | | | 1.0 | 0.0 |
| | SUGARBEETS | | | 5.7 | 4.0 |
| | CORN,FIELD | | | 0.3 | 0.0 |
| | COTTON | | | 8.3 | 6.0 |
| | RICE,NATO | | | 2.3* | 0.0 |
| | SOYBEAN,ADELPHIA | | | 8.3 | 6.0 |
| | SUNFLOWER,UNSPECIFIE | | | 4.0 | 2.3 |
| | WHEAT,SPRING,ERA | | | 1.0 | 0.0 |

TABLE XIV

Preemergence herbicidal evaluation of test compounds

| Compound | Plant Species | Rates in kg/ha | | | |
|---|---|---|---|---|---|
| | | 8.0 | 5.0 | 2.0 | 1.0 |
| 1-Nitro-3-[α-(trifluoromethyl)benzyl]-guanidine | BARNYARDGRASS | | 8.0 | | |
| | CRABGRASS,(HAIRY) L | | 7.0 | | |
| | FOXTAIL,GREEN | | 7.0 | | |
| | NUTSEDGE,PURPLE | | 6.0 | | |
| | OAT,WILD | | 2.0 | | |
| | QUACKGRASS | | 0.0 | | |
| | BINDWEED,FIELD (RHIZ) | | 9.0 | | |
| | MORNINGGLORY SPP. | | 8.0 | | |
| | MUSTARD,WILD | | 8.0 | | |
| | RAGWEED,COMMON | | 8.0 | | |
| | SIDA,PRICKLY | | 9.0 | | |
| | VELVETLEAF | | 8.0 | | |

TABLE XV

Preemergence herbicidal evaluation of test compounds

| Compound | Plant Species | Rates in kg/ha | | | |
|---|---|---|---|---|---|
| | | 8.0 | 4.0 | 2.0 | 1.0 |
| 1-(o-Fluoro-α-methylbenzyl)-3-nitroguanidine | BARNYARDGRASS | 6.0 | | | |
| | CRABGRASS,(HAIRY) L | 0.0 | | | |
| | FOXTAIL,GREEN | 5.0 | | | |
| | QUACKGRASS | 0.0 | | | |
| | BINDWEED,FIELD (RHIZ) | 9.0 | | | |
| | MUSTARD,WILD | 7.0 | | | |
| | RAGWEED,COMMON | 9.0 | | | |
| | SIDA,PRICKLY | 8.0 | | | |
| | VELVETLEAF | 9.0 | | | |

TABLE XVI

Preemergence herbicidal evaluation of test compounds

| Compound | Plant Species | Rates in kg/ha | | | |
|---|---|---|---|---|---|
| | | 8.0 | 4.0 | 2.0 | 1.0 |
| 1-(p-Fluoro-α-methylbenzyl)-3-nitroguanidine | BARNYARDGRASS | 7.0 | | | |
| | CRABGRASS,(HAIRY) L | 0.0 | | | |
| | FOXTAIL,GREEN | 3.0 | | | |
| | NUTSEDGE,PURPLE | 0.0 | | | |
| | QUACKGRASS | 0.0 | | | |
| | BINDWEED,FIELD (RHIZ) | 8.0 | | | |
| | MORNINGGLORY SPP. | 4.0 | | | |
| | MUSTARD,WILD | 8.0 | | | |
| | RAGWEED,COMMON | 7.0 | | | |
| | SIDA,PRICKLY | 9.0 | | | |
| | VELVETLEAF | 6.0 | | | |

TABLE XVII

Preemergence herbicidal evaluation of test compounds

| Compound | Plant Species | Rates in kg/ha | | | |
|---|---|---|---|---|---|
| | | 8.0 | 4.0 | 2.0 | 1.0 |
| (−)-1-(α-Ethylbenzyl)-3-nitroguanidine | BARNYARDGRASS | 6.0 | | | |
| | CRABGRASS,(HAIRY) L | 7.0 | | | |
| | FOXTAIL,GREEN | 7.0 | | | |
| | NUTSEDGE,PURPLE | 3.0 | 0.0 | 0.0 | |
| | OAT,WILD | 2.0 | | | |
| | QUACKGRASS | 4.0 | 3.0 | 0.0 | |
| | BINDWEED,FIELD (RHIZ) | 9.0 | 0.0 | 0.0 | |
| | COCKLEBUR | | 0.0 | 0.0 | |
| | LAMBSQUARTERS,COMMO | | 0.0 | 0.0 | |
| | MORNINGGLORY SPP. | 6.0 | 0.0 | 0.0 | |
| | MUSTARD,WILD | 7.0 | 0.0 | 0.0 | |
| | PIGWEED,REDROOT | | 0.0 | 0.0 | |
| | RAGWEED,COMMON | 9.0 | 0.0 | 0.0 | |
| | SIDA,PRICKLY | 9.0 | | | |
| | SMARTWEED,PENNSYLVA | | 0.0 | 0.0 | |
| | VELVETLEAF | 7.0 | 3.0 | 0.0 | |
| | WHEAT,WINTER,FENMA | | 0.0 | 0.0 | |
| | BARLEY,SPRING,LARKER | | 0.0 | 0.0 | |
| | CORN,FIELD | | 0.0 | 0.0 | |
| | RICE,NATO | | 0.0 | 0.0 | |
| | SORGHUM,GRAIN | | 0.0 | 0.0 | |

TABLE XVIII

Preemergence herbicidal evaluation of test compounds

| Compound | Plant Species | Rates in kg/ha | | | |
|---|---|---|---|---|---|
| | | 8.0 | 4.0 | 2.0 | 1.0 |
| (+)-1-Cyano-3-(α-ethylbenzyl)-guanidine | NUTSEDGE,PURPLE | | | 3.0 | 3.0 |
| | QUACKGRASS | | | 4.0 | 0.0 |
| | BINDWEED,FIELD (RHIZ) | | | 9.0 | 9.0 |
| | COCKLEBUR | | | 8.0 | 2.0 |
| | LAMBSQUARTERS,COMMO | | | 9.0 | 9.0 |
| | MORNINGGLORY SPP. | | | 6.0 | 4.0 |
| | MUSTARD,WILD | | | 8.0 | 7.0 |
| | PIGWEED,REDROOT | | | 9.0 | 7.0 |
| | RAGWEED,COMMON | | | 4.0 | 0.0 |
| | SMARTWEED,PENNSYLVA | | | 2.0 | 0.0 |
| | VELVETLEAF | | | 8.0 | 7.0 |
| | WHEAT,WINTER,FENMA | | | 0.0 | 0.0 |
| | BARLEY,SPRING,LARKER | | | 0.0 | 0.0 |
| | CORN,FIELD | | | 3.0 | 2.0 |
| | RICE,NATO | | | 3.0 | 3.0 |
| | SORGHUM,GRAIN | | | 3.0 | 0.0 |

What is claimed is:

1. A method for the preemergence control of undesirable broadleaf weeds and grass plants comprising, applying to soil containing seeds or other propagating organs of said undesirable braodleaf weeds and grass plants a herbicidally effective amount of a substituted nitroguanidine or cyanoguanidine compound selected from the group consisting of

wherein $R_1$ is $NO_2$ or $CN$; $R_2$ is $n-C_3H_7$, $CH_2OCH_3$ or $CH_2CH=CH_2$; X is hydrogen, o-F, m-F, p-F, m-OCH$_3$, m-OH or p-Cl; the salts, tautomers and optical isomers thereof and the (+) or (−)-isomers of compounds having the above structure, wherein $R_1$ and X are as described and $R_2$ is $CH_3$, $C_2H_5$ or $CF_3$.

2. A method according to claim 1, wherein said compound is applied to soil at a rate of from about 1.0 to 10.0 kg/ha and is 1-[α-(methylmethoxy)-benzyl]-3-nitroguanidine; 1-(α-ethylbenzyl)-3-nitroguanidine; 1-nitro-3-[α-(trifluoromethyl)benzyl]guanidine; (−)1-(α- ethylbenzyl)-3-nitroguanidine; (+)-1-(α-ethylbenzyl)-3-nitroguanidine; 1-nitro-3-(α-propylbenzyl)guanidine; 6-1-(α-allylbenzyl)-3-nitroguanidine; (+)-α-methylbenzyl)-3-nitroguanidine; 1-(α-ethyl-m-methoxybenzyl)-3-nitroguanidine; 1-(α-ethyl-m-fluorobenzyl)-3-nitroguanidine; 1-(α-ethyl-p-fluorobenzyl)-3-nitroguanidine; 1-(m-chloro-α-ethylbenzyl)-3-nitroguanidine; or 1-cyano-3-(α-ethylbenzyl)guanidine.

3. A method for the preemergence control of undesirable broadleaf weeds and grass plants in the presence of graminaceous crops comprising, applying to soil planted with seed of graminaceous crops and containing seeds or other propagating organs of said undesirable broadleaf weeds and grass plants, about 1.0 to 4.00 kg/ha of a compound having the formula

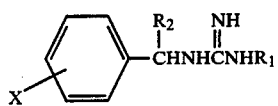

wherein $R_1$ is $NO_2$ or CN; $R_2$ is n-$C_3H_7$, $CH_2OCH_3$ or $CH_2CH=CH_2$; X is hydrogen, o-F, m-F, p-F, m-$OCH_3$, m-OH or p-Cl; and the salts, tautomers and optical isomers thereof and the (+) and (−)-isomers of compounds having the above structure, wherein $R_1$ and X are as described and $R_2$ is $CH_3$, $C_2H_5$ or $CF_3$.

4. A method according to claim 3, wherein the compound is 1-[α-(methoxymethyl)benzyl]-3-nitroguanidine.

5. A method according to claim 3, wherein the compound is 1-nitro-3-(α-n-propylbenzyl)guanidine.

6. A method according to claim 3, wherein the compound is 1-(α-allylbenzyl)-3-nitroguanidine.

7. A method according to claim 3, wherein the compound is (−)-1-(α-ethylbenzyl)-3-nitroguanidine.

8. A method according to claim 3, wherein the compound is (+)-1-(α-ethylbenzyl)-3-nitroguanidine.

9. A method according to claim 3, wherein the compound is (+)-1-(α-methylbenzyl)-3-nitroguanidine.

10. A method according to claim 3, wherein the compound is (+)-1-cyano-3-(α-ethylbenzyl)guanidine.

* * * * *